United States Patent [19]
Van Zile et al.

[11] Patent Number: 5,147,405
[45] Date of Patent: Sep. 15, 1992

[54] KNEE PROSTHESIS

[75] Inventors: Richard Van Zile; Donald McNulty; James Caywood, all of Warsaw, Ind.

[73] Assignee: Boehringer Mannheim Corporation, Indianapolis, Ind.

[21] Appl. No.: 728,016

[22] Filed: Jul. 8, 1991

Related U.S. Application Data

[63] Continuation of Ser. No. 477,037, Feb. 7, 1990, abandoned.

[51] Int. Cl.$^5$ ............................................. A61F 2/38
[52] U.S. Cl. ........................................................ 623/20
[58] Field of Search ............................ 623/16, 18, 19, 20, 623/23

[56] References Cited

U.S. PATENT DOCUMENTS

| | | |
|---|---|---|
| 4,001,896 | 1/1977 | Arkangel ............................ 623/20 |
| 4,209,861 | 7/1980 | Walker et al. ....................... 623/20 |
| 4,213,209 | 7/1980 | Insall et al. ......................... 623/20 |
| 4,224,697 | 9/1980 | Murray et al. ....................... 623/20 |
| 4,249,270 | 2/1981 | Bahler et al. ........................ 623/20 |
| 4,257,129 | 3/1981 | Volz . | |
| 4,298,992 | 11/1981 | Burstein et al. ..................... 623/20 |
| 4,309,778 | 1/1982 | Buechel et al. ..................... 623/20 |
| 4,340,978 | 7/1982 | Buechel et al. ..................... 623/20 |
| 4,470,158 | 9/1984 | Pappas et al. ....................... 623/20 |
| 4,501,031 | 2/1985 | McDaniel et al. ................... 623/20 |
| 4,634,444 | 1/1987 | Noiles .................................. 623/20 |
| 4,795,468 | 1/1989 | Hodorek et al. ..................... 623/20 |
| 4,892,547 | 1/1990 | Brown ................................. 623/20 |
| 5,007,933 | 4/1991 | Sidebotham et al. ................ 623/20 |

FOREIGN PATENT DOCUMENTS 2223900  4/1990  United Kingdom ................ 623/20

*Primary Examiner*—David Isabella
*Attorney, Agent, or Firm*—Barnes & Thornburg

[57] ABSTRACT

A knee prosthesis is provided including a tibial component having first and second generally concave bearing surfaces and a stabilizing post extending upwardly between the first and second bearing surfaces. The knee prosthesis also includes a femoral component having first and second spaced apart, convexly curved condyle bearing surfaces and a cam surface extending between the first and second bearing surfaces. The femoral component is articulatable with the tibial component between an extended position and a flexed position. The first and second femoral bearing surfaces engage the first and second tibial bearing surfaces, respectively, at first and second contact points. Between the extended position and about a 25° flexion angle, the cam surface is spaced apart from a posterior side wall of the stabilizing post to permit movement of the femoral and tibial component as natural physiology dictates. As the knee prosthesis is flexed at about a 25° flexion angle, the cam surface first engages the posterior side wall of the stabilizing post to control movement of the femoral component relative to the tibial component. Therefore, the stabilizing post engages the cam surface to control the position of the femoral component relative to the tibial component only upon flexion of the femoral and tibial component between about 25° flexion and the flexed position.

20 Claims, 3 Drawing Sheets

KNEE PROSTHESIS

CROSS REFERENCE TO RELATED APPLICATION

This application is a continuation of U.S. application Ser. No. 07/477,037 filed Feb. 7, 1990, now abandoned.

BRIEF DESCRIPTION OF THE DRAWINGS

The present invention relates to a prosthesis for replacing a natural knee joint. More particularly, the present invention relates to a posterior stabilized knee prosthesis assembly including a femoral component and a tibial component for use in a total knee joint replacement procedure.

During treatment of diseased and damaged knee joints, surgery is often necessary to attempt to repair the knee. If the damaged or diseased knee cannot be surgically repaired, total replacement of the knee with a knee prosthesis is often required. In conventional prosthetic knee assemblies, it is known to provide a femoral component designed to be attached to a resected femur which articulates with a tibial component designed to be attached to a resected tibia by a tibial tray.

Figure 1:
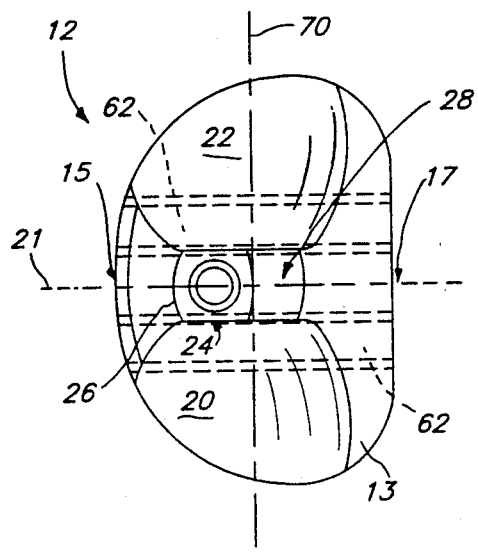

Femoral components typically include a pair of spaced apart bearing surfaces or condyles which replace a natural femoral condyle. Tibial components typically include a platform portion having a pair of spaced apart bearing surfaces which respectively engage the spaced apart bearing surfaces of femoral component. The femoral and tibial components, which articulate between an extended position and a flexed position, replace a natural knee joint.

One feature associated with conventional prosthetic knee assemblies is the large amount of "rollback" which occurs upon flexion of the femoral and tibial components. Rollback is the distance that contact points between the bearing surfaces of the femoral and tibial components move in the posterior direction past an imaginary center line located midway between the anterior and posterior ends of the tibial component upon flexion of the knee. A large amount of rollback can cause flexing or "rocking" of the tibial tray used to secure the tibial component to the tibia. Flexing or rocking of the tibial tray can loosen the tibial tray over time. Once the tibial tray becomes loose, it must be replaced.

Another feature associated with conventional prosthetic knee assemblies is that rollback occurs as the flexion angle between the femoral and tibial components approaches the flexed position. This "late" rollback can cause impingement or pinching of soft tissue located behind the posterior side of the prosthetic knee assembly. Pinching of the soft tissue is likely to occur between the bearing surfaces of the femoral and tibial components when the contract points between the bearing surfaces move in the posterior direction as the flexion angle approaches the flexed position.

Yet another feature associated with conventional prosthetic knee assemblies is that the femoral component can become dislocated from the tibial component during normal activities such as going up or down stairs in which the knee is flexed at an angle of approximately 30°.

One object of the present invention is to provide a knee prosthesis which closely replicates the function of a natural knee.

Another object of the present invention is to reduce the likelihood that the tibial tray for securing the tibial component to the tibia will become loose after the tibial tray is attached to the tibia.

Yet another object of the present invention is to reduce the likelihood of impingement of the soft tissue located on the posterior side of the knee prosthesis.

Still another object of the present invention is to reduce the likelihood that the femoral and tibial components will become dislocated during function of the knee prosthesis.

According to the present invention, the knee joint prosthesis is provided for replacing a natural knee joint. The knee joint prosthesis includes a femoral component having first and second spaced apart, convexly curved condyle bearing surfaces and a posterior cam surface extending between the first and second bearing surfaces. The knee joint prosthesis also includes a tibial component. The femoral component is articulatable with the tibial component between an extended position and a flexed position. The tibial component includes an anterior/posterior axis and first and second bearing surfaces for engaging the first and second bearing surfaces of the femoral component, respectively, at first and second contact points located at substantially equal positions relative to the anterior/posterior axis of the tibial component. The tibial component also includes means for engaging the posterior cam surface of the femoral component to control the position of the femoral component relative to the tibial component only upon flexion of the femoral and tibial components between about 25° flexion and the flexed position. The posterior cam surface of the femoral component is spaced apart from the engaging means upon flexion of the femoral and tibial components between the extended position and about 25° flexion.

The contact points between the first and second bearing surfaces of the femoral and tibial components move in the posterior direction relative to the tibial component upon flexion of the femoral and tibial components from about 25° to about 45° flexion due to contact of the posterior cam surface and the engaging means. During flexion from about a 45° flexion angle to the flexed position, the contact points remain in a constant dwell position relative to the tibial component. Therefore, no rollback occurs upon flexion of the femoral and tibial components from about 45° to the flexed position. The total distance of rollback of the contact points is about 6 mm.

The total distance of movement of the contact points in the posterior direction upon flexion of the femoral and tibial components from the extended position to the flexed position is less than 9 mm. By limiting the range of movement of the contact points relative to the tibial component to less than 9 mm, the asymmetric distribution of forces on the center of the tibial tray used to secure the tibial component to a tibia bone is limited.

Tibial trays typically include a stem located somewhere near the center of the tray which extends into the tibia to secure the tray to the tibia. By minimizing the amount of rollback of the contact points and maintaining the contact points substantially near the center of the tibial tray during flexion of the femoral and tibial components, the present invention reduces the likelihood of flexing or rocking of the tibial tray about its attachment stem. Advantageously, this reduces the likelihood that the tibial tray will become loose from the tibia and require replacement.

By causing rollback of the contact points relative to the tibial component only between about a 25° flexion angle and about a 45° flexion angle, the knee prosthesis of the present invention reduces the likelihood of impingement of soft tissue located on the posterior side of the femoral and tibial components. Such soft tissue impingement typically occurs when rollback of the contact points occurs near the flexed position of the femoral and tibial components.

In a preferred embodiment of the present invention, the engaging means includes a stabilizing post having a posterior side wall. The posterior side wall provides a generally convex contact surface for engaging a generally concave contact surface of the posterior cam surface. The posterior side wall has a first inferior section which slopes downwardly in the posterior direction for engaging the generally concave contact surface of the posterior cam surface of the femoral component. The sloped inferior section of the posterior side wall controls the position of the femoral component relative to the tibial component upon flexion of the femoral and tibial components between about a 25° flexion angle and the flexed position.

The stabilizing post also includes a second superior section aligned generally perpendicularly to the first and second bearing surfaces of the tibial component. The second superior section of the posterior side wall engages the posterior cam surface of the femoral component upon posterior movement of the tibial component relative to the femoral component to prevent dislocation of the femoral and tibial components. This two-section posterior side wall Provides added resistance to posterior tibial component subluxation or dislocation. This feature advantageously reduces the likelihood that the femoral component will slide off the tibial component during operation of the knee prosthesis.

An anchoring rod extends through the stabilizing post of the tibial component and into the tibial tray used to secure the tibial component to a tibia. The anchoring rod secures the tibial component to the tibial tray and strengthens the stabilizing post. By strengthening the stabilizing post, this feature advantageously further reduces the likelihood that the femoral and tibial components will become dislocated during operation of the knee prosthesis.

The femoral component includes an anterior cam surface extending between the first and second bearing surfaces of the femoral component spaced apart from the posterior cam surface in the anterior direction. The stabilizing post of the tibial component includes an anterior side wall for engaging the anterior cam surface of the femoral component upon hyperextension of the femoral and tibial components. Engagement of the anterior cam surface with the anterior side wall prevents posterior movement of the femoral component with respect to the tibial component upon hyperextension of the femoral and tibial components.

Additional objects, features, and advantages of the invention will become apparent to those skilled in the art upon consideration of the following detailed description of a preferred embodiment exemplifying the best mode of carrying out the invention as presently perceived.

BRIEF DESCRIPTION OF THE DRAWINGS

Figure 2:
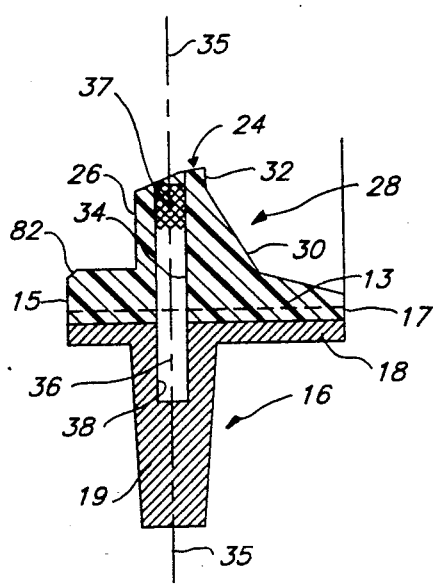
Figure 3:
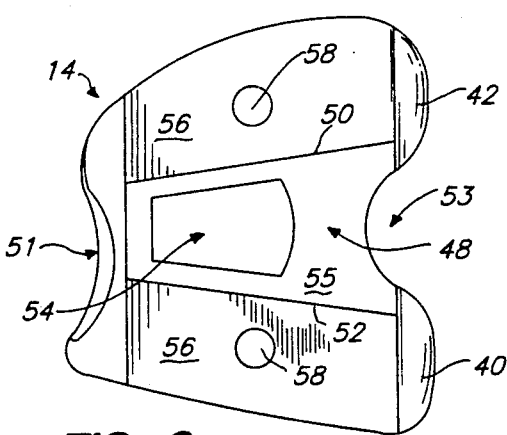
Figure 4:
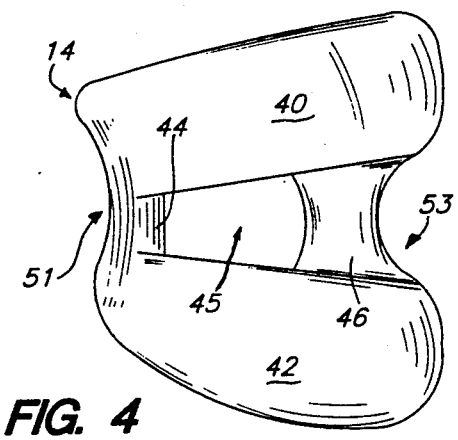
Figure 5:
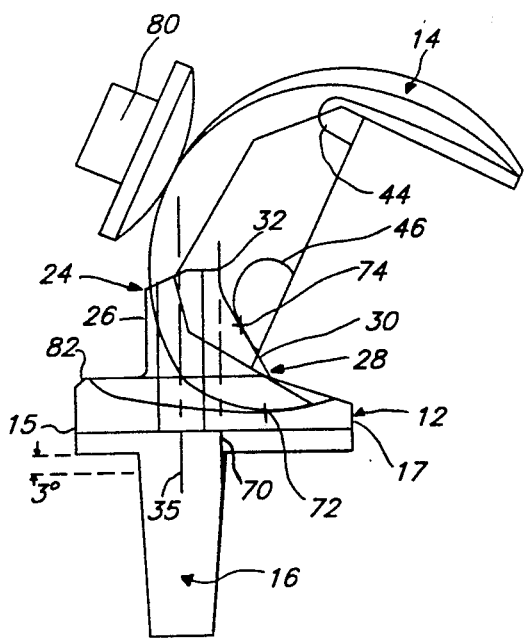
Figure 6A:
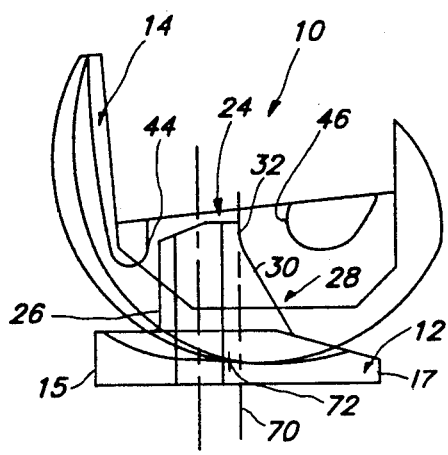
Figure 6B:
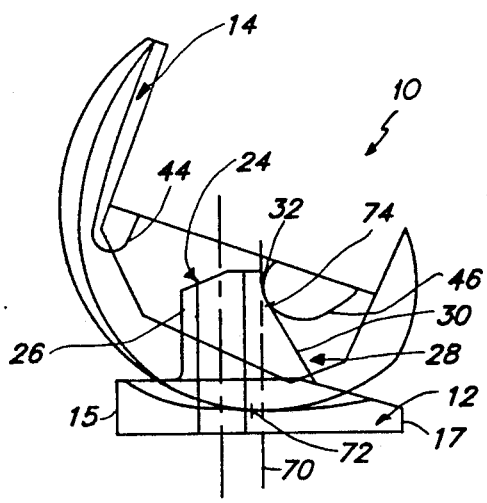
Figure 6C:
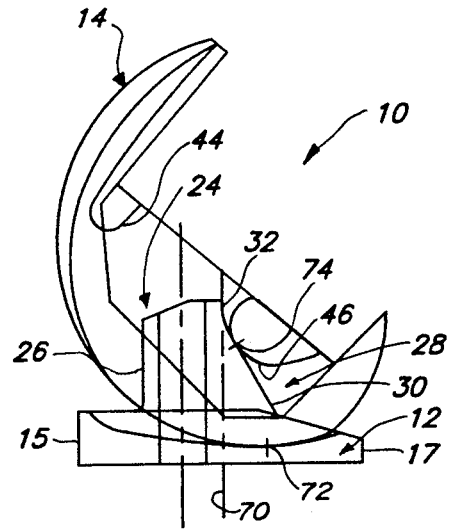
Figure 6D:
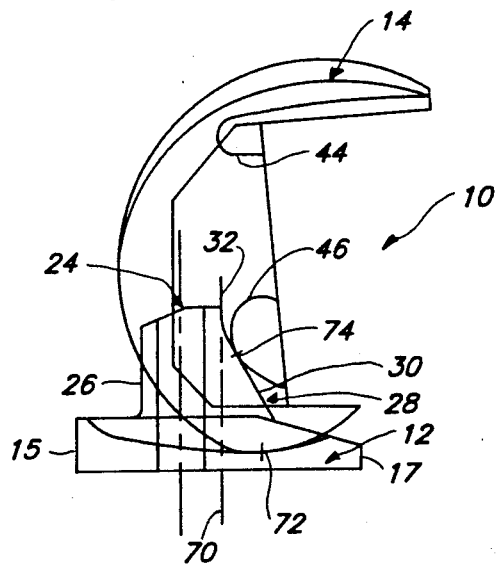
Figure 6E:
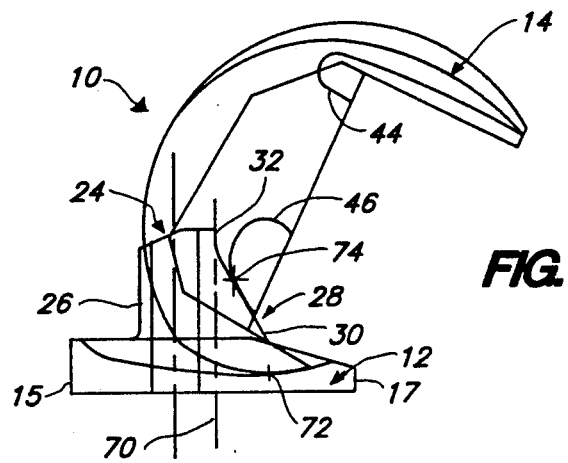
Figure 6F:
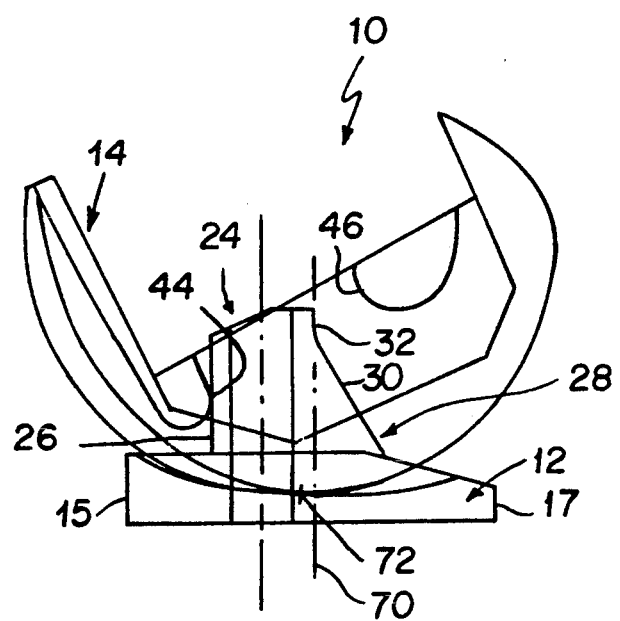

The detailed description particularly refers to the accompanying figures in which:

FIG. 1 is a plan view of a tibial component of the knee prosthesis of the present invention;

FIG. 2 is a sectional view illustrating the tibial component attached to a tibial tray, a stabilizing post extending away from the superior surface of the tibial component, and a rod extending through the stabilizing post of the tibial component and into the tibial tray;

FIG. 3 is a plan view of a femoral component of the knee prosthesis of the present invention;

FIG. 4 is a bottom view of the femoral component shown in FIG. 3;

FIG. 5 is a schematic sectional view of the femoral component and the tibial component in a flexed position illustrating the position of an artificial patella movable along the anterior portion of the knee prosthesis;

FIG. 6a is a schematic sectional view of the knee prosthesis when the femoral component and the tibial component are situated in an extended position at a flexion angle of about 0°;

FIG. 6b is a schematic sectional view illustrating the femoral and tibial components flexed at an angle of about 25°;

FIG. 6c is a schematic sectional view illustrating the femoral and tibial components flexed at an angle of about 45°;

FIG. 6d is a schematic sectional view illustrating the femoral and tibial components flexed at an angle of about 90°; and FIG. 6e is a schematic sectional view illustrating the femoral and tibial components situated in a flexed position at an angle of about 120°; and FIG. 6f is a schematic sectional view where the anterior surface on the stabilizing post controls relative positioning between the tibial and fibial component.

DETAILED DESCRIPTION OF THE DRAWINGS

The knee prosthesis 10 of the present invention includes a tibial component 12 and a femoral component 14. The tibial component 12 is designed to be secured to an upper extremity of a resected tibia (not shown) by a suitable tibial tray 16 as best shown in FIG. 2. Tibial tray 16 includes a generally planar tray portion 18 and a stem portion 20 for anchoring the tibial tray 16 to the tibia.

The tibial component 12 includes an anterior end 15, a posterior end 17, and an anterior/posterior axis 21 extending between the anterior and posterior ends 15 and 17. Tibial component 12 also includes first and second spaced apart, generally concave bearing surfaces 20 and 22 and a stabilizing post 24 extending upwardly in the superior direction between the first and second bearing surfaces 20 and 22. Tibial component 12 is preferably formed from a polymeric material such as ultra high molecular weight polyethylene (UHMWPE).

Stabilizing post 24 includes an anterior side wall 26 and a posterior side wall 28. As best shown in FIG. 2, posterior side wall 28 includes a first inferior section 30 sloped downwardly in the posterior direction toward posterior end 17 at an angle of about 33° with respect to an inferior superior axis 35 of stabilizing post 24. The inferior section 30 of posterior side wall 28 engages a posterior cam surface 46 of femoral component 14 to control movement of femoral component 14 relative to tibial component 12 upon flexion of the femoral and tibial components 14 and 12 between about a 25° flexion angle and the flexed position.

Posterior side wall 28 also includes a second superior section 32 located above inferior section 30. Superior section 32 is aligned generally perpendicularly to the generally planar platform 13 of tibial component 12 and to the first and second bearing surfaces 20 and 22. Superior section 32 is substantially parallel to the inferior/superior axis 35 of stabilizing post 24.

Stabilizing post 24 is formed to include an aperture 34 extending along the inferior/superior axis 35. Aperture 34 is formed to receive a pin or rod 36 which extends through the aperture 34 of stabilizing post 24 and into an aperture 38 formed in the tibial tray 16. The rod 36 strengthens and stabilizes stabilizing post 24 and helps to secure tibial component 12 to tibial tray 16.

Preferably, rod 36 is made from a high strength material such as a cobalt-chromium base alloy. Rod 36 is approximately 5/16 inch in diameter and is press fit into aperture 38 of tibial tray 16. The top portion 37 of the rod 36 located inside aperture 34 of stabilizing post 24 is knurled to strengthen the engagement between rod 36 and stabilizing post 24.

Tibial component 12 includes a center line 70 located along a medial/lateral axis of tibial component 12 midway between anterior end 15 and posterior end 17 of tibial component 12. Center line 70 is positioned above a medial/lateral axis (not shown) through the center of a tibia bone (not shown) when the tibial component 12 is connected to the tibia (not shown) by tibia tray 16. Tibial component 12 also includes a pair of spaced apart grooves 62 formed on the inferior side of tibial component 12. The pair of grooves 62 receive first and second slide members (not shown) on tibial tray 16 to secure tibial component 12 on tibial tray 16. It is understood that tibial component 12 can be attached to tibial tray 16 in any conventional manner.

The femoral component 14 of knee prosthesis 10 is best shown in FIGS. 3 and 4. Femoral component 14 includes first and second diverging condyles or bearing surfaces 40 and 42. First and second bearing surfaces 40 and 42 are spaced apart and are convexly curved to match the curvature of natural pair of femoral condyles. An anterior cam surface 44 and a posterior cam surface 46 extend between the first and second bearing surfaces 40 and 42 to lie in an intercondylar region 45 as best shown in FIG. 4. Posterior cam surface 46 includes a generally concave contact surface having the shape of a hyperboloid.

Femoral component 14 is left and right side specific. The femoral component 14 shown in FIGS. 3 and 4 is designed for use on the right knee of the body. The use of left and right specific knees more closely replicates a natural knee. In addition, the present knee configuration increases the flexibility of the knee for medial/lateral rotation of the femoral and tibial components 14 and 12.

FIG. 3 illustrates the superior side of femoral component 14 which includes an intercondylar box 48 extending between the first and second bearing surfaces 40 and 42. Intercondylar box 48 includes first and second spaced apart, upstanding side walls 50 and 52 which diverge from the posterior end 53 to the anterior end 51 of femoral component 14.

Intercondylar box 48 houses stabilizing post 24 of tibial component 12 when the tibial and femoral components 12 and 14 are engaged. The top surface 55 is formed to include an aperture 54 extending between anterior cam surface 44 and posterior cam surface 46. Aperture 54 permits intercondylar box 48 to have lower height or profile. This low profile of the intercondylar box 48 reduces the amount of bone that must be removed from a femur (not shown) to install femoral component 14.

Intercondylar box 48 is situated between first and second surfaces 56 which abut the exposed surface of the resected femur (not shown). A pin member 58 extends upwardly from each of the surfaces 56. Pin members 58 are inserted into appropriately formed holes in the resected surface of the femur (not shown) to facilitate positioning femoral component 14 on the femur (not shown). Femoral component 14 is preferably integrally cast from a suitable metal surgical implant alloy such as a cobalt-chromium alloy.

The operation of the knee prosthesis 10 with femoral component 14 and tibial component 12 in an engaged position is best shown in FIGS. 6a–6e. The first and second bearing surfaces 40 and 42 of femoral component 14 engage the first and second bearing surfaces 20 and 22, respectively, of tibial component 12 at first and second contact points 72. The contact points 72 are located at substantially equal positions relative to an anterior/posterior axis 21 of tibial component 12.

The curvature of concave bearing surfaces 20 and 22 of tibial component 12 is different than the curvature of bearing surfaces 40 and 42 of femoral component 14. Therefore, the contact between bearing surfaces 20 and 22 and bearing surfaces 40 and 42, respectively, occurs only at substantially single contact points 72 located on each side of the anterior/posterior axis 21 as indicated by location 72 on FIGS. 6a–6e.

Femoral component 14 and tibial component 12 are articulatable between an extended position shown in FIG. 6a and a flexed position shown in FIG. 6e. Tibial component 12 and femoral component 14 can also be hyperextended somewhat. When femoral component 14 and tibial component 12 are hyperextended beyond about 5°, anterior cam surface 44 of femoral component 14 engages anterior side wall 26 of stabilizing post 24 (FIG. 6f).

When femoral component 14 and tibial component 12 are situated from about 4° hyperextension to about a 24° flexion angle, the anterior cam surface 44 and the posterior cam surface 46 are spaced apart from the anterior side wall 26 and posterior side wall 28, respectively, of stabilizing post 24. During this range of flexion, (−4° to +24° flexion) tibial component 12 and femoral component 14 are free to move as natural physiology dictates. FIG. 6a illustrates the position of femoral component 14 and tibial component 12 when situated in the extended position or at a 0° flexion angle. Neither anterior cam surface 44 nor posterior cam surface 46 engage stabilizing post 24 when femoral component 14 and tibial component 12 are in the extended position.

In FIGS. 6a–6e, line 70 illustrates the position of the center line 70 of tibial component 12. Line 72 illustrates the position of the contact points 72 between the first and second bearing surfaces 40 and 42 of femoral component 14 and the first and second bearing surfaces 20 and 22 of tibial component 12, respectively.

As the knee prosthesis 10 is flexed, as shown successively in FIGS. 6a through 6e, femoral component 14 rotates in a clockwise direction as viewed in the drawings with respect to tibial component 12. As the knee prosthesis 10 is flexed at about a 25° flexion angle as shown in FIG. 6b, posterior cam surface 46 of femoral component 14 first engages the inferior section 30 of posterior side wall 28 of stabilizing post 24. The position of the contact or engagement between posterior cam surface 46 and inferior section 30 of posterior side wall 28 is illustrated by location 74.

During flexion of the knee prosthesis 10 from an angle of about 25° to the flexed position, posterior cam surface 46 of femoral component 14 controls movement of the contact points 72 relative to tibial component 12. When femoral component 14 and tibial component 12 are flexed at about 25°, the contact points 72 are situated toward the anterior end 15 of tibial component 12 from center line 70 by about 2.3 mm. Therefore, inferior section 30 of stabilizing post 24 provides means for engaging the posterior cam surface 46 of femoral component 14 to control the position of femoral component 14 relative to tibial component 12 only upon flexion of the femoral and tibial components 14 and 12 between about 25° and the flexed position.

During normal activity, stresses on the knee prosthesis 10 tend to force femoral component 14 to slide along the anterior/posterior axis 21 of tibial component 12. One of the normal activities that causes the most stress on the knee is climbing or descending stairs. When descending stairs, the femoral and tibial components 14 and 12 are typically flexed at about a 30° flexion angle and forces on the knee make it likely that the femoral component 14 will slide in the anterior direction relative to the tibial component 12. The knee prosthesis 10 of the present invention provides posterior support to prevent dislocation of the femoral and tibial components 14 and 12 at the critical 30° flexion angle.

At about a 30° flexion angle, posterior cam surface 46 is engaged with inferior section 30 of posterior side wall 28 to provide resistance to movement of femoral component 14 in the anterior direction relative to tibial component 12. The vertical superior section 32 of stabilizing post 24 provides even stronger resistance to anterior movement of femoral component 14 should femoral component 14 slide up inferior section 30. At about a 30° flexion angle, the contact points 72 are located directly on center line 70 to provide maximum stability for the knee prosthesis 10 at the critical 30° flexion angle.

As femoral component 14 continues to rotate in the clockwise direction relative to tibial component 12, contact points 72 move in the posterior direction. When femoral component 14 and tibial component 12 are flexed at an angle of about 45°, as shown in FIG. 6c, contact points 72 have moved to a location about 6 mm in the posterior direction of center line 70. This location of contact points 72 shown in FIG. 6c is the maximum rollback distance of contact points 72. Therefore, rollback of contact points 72 caused by posterior cam surface 46 and the inferior section 30 occurs only between the 25° position of FIG. 6b and the 45° position of FIG. 6c. This reduces the likelihood of impingement of soft tissue located in the posterior direction of knee prosthesis 10. Of course there may be some small movement of the contact points 72 and the tibial bearing surfaces 20, 22 due to natural tissue interaction from the extended position shown in FIG. 6a to the 25° position of FIG. 6b. This movement from 0° to 25° flexion, however, is not caused by engagement of cam surface 46 and inferior section 30.

As femoral component 14 continues to rotate with respect to tibial component 12 in the clockwise direction to a flexion angle of about 90° as shown in FIG. 6d, contact points 72 remain in a constant dwell position 72 relative to tibial component 12. The total distance of movement of the contact points 72 in the posterior direction upon flexion of the femoral and tibial components 14 and 12 from the extended position (FIG. 6a) to the flexed position (FIG. 6e) is less than 9 mm total or less than 6 mm from the center line 70. By maintaining the contact points 72 in close proximity to center line 70, the present invention reduces the likelihood of flexing or rocking the tibial tray 16 used to secure tibial component 12 to the tibia. Therefore, the present invention reduces the likelihood that the tibial tray 16 will become loose after it is attached to the tibia (not shown).

FIG. 6e illustrates the knee prosthesis 10 and the contact points 72 when the femoral component 14 and the tibial component 12 are in the flexed position at an angle of about 120°. Contact points 72 remain in the same position relative to tibial component 12 between flexion angles of about 45° and the flexed position of about 120°.

The specific position of the contact points 72 relative to center line 70 are shown in the following table. The extended position of the femoral and tibial components 14 and 12 shown in FIG. 6a corresponds to a 0° flexion angle. A negative flexion angle indicates hyperextension of knee prosthesis 10. A positive contact position indicates that the contact points 72 are located on the posterior side of center line 70. A negative contact position indicates that the contact points 72 are located on the anterior side of center line 70.

| Flexion Angle (degrees) | Contact Position (mm) |
| --- | --- |
| −5 | −2.7 |
| −4 to 24 | free to move as physiology dictates |
| 25 | −2.3 |
| 30 | 0 |
| 40 | +4.3 |
| 45–120 | +6.0 |

FIG. 5 illustrates the position of an artificial patella 80 which moves between first and second bearing surfaces 40 and 42 of femoral component 14 upon flexion of knee prosthesis 10. By limiting the rollback of the contact points 72 with respect to tibial component 12 to 6 mm, the present invention prevents the anterior side wall 26 of stabilizing post 24 from extending substantially beyond the first or second bearing surfaces 40 or 42 of femoral component 14. This prevents the patella 80 from striking the stabilizing post 24 during flexion of knee prosthesis 10. The anterior end 15 of tibial component 12 includes a chamfer 82 to prevent contact of patella 80 with a sharp edge. Therefore, the present invention reduces the likelihood that the patella 80 will break down and require replacement.

FIG. 5 also illustrates that the planar tray portion 18 of tibial tray 16 is aligned at about 3° with respect to horizontal when attached to the tibia (not shown). A suitable cutting tool (not shown) is used to cut the top of the tibia at the 3° slope.

Although the invention has been described in detail with reference to a preferred embodiment, variations and modifications exist within the scope and spirit of the invention as described and defined in the following claims.

What is claimed is:

1. A knee joint prosthesis comprising:
   a femoral component including first and second spaced apart, convexly curved condyle bearing surfaces and a cam surface extending between the first and second bearing surfaces; and a tibial component, the femoral component being articulatable with the tibial component between an extended position and a flexed position, the tibial component including first and second bearing surfaces for engaging the first and second bearing surfaces of the femoral component, respectively, and means for engaging the cam surface of the femoral component to control the position of the femoral component relative to the tibial component only upon flexion of the femoral and tibial components between about 25 degrees and the flexed position, the cam surface being spaced apart from the engaging means upon flexion of the femoral and tibial components between the extended position and about 25 degrees, and wherein the control provides for a point of contact between the femoral and tibial components to move in a posterior direction from about 25 degrees through 45 degrees and to remain substantially unchanged from about 45 degrees to the flexed position.

2. A knee joint prosthesis comprising:

a femoral component including first and second spaced apart, convexly curved condyle bearing surfaces and a cam surface extending between the first and second bearing surfaces; and a tibial component, the femoral component being articulatable with the tibial component between an extended position and a flexed position, the tibial component including first and second bearing surfaces for engaging the first and second bearing surfaces of the femoral component, respectively, and means for engaging the cam surface of the femoral component to control the position of the femoral component relative to the tibial component only upon flexion of the femoral and tibial components between about 25 degrees and the flexed position, the cam surface being spaced apart from the engaging means upon flexion of the femoral and tibial components between the extended position and about 25 degrees, wherein the tibial component includes an anterior/posterior axis and the first and second bearing surfaces of the femoral component engage the first and second bearing surfaces of the tibial component, respectively, at first and second contact points located at substantially equal positions relative to the anterior/posterior axis of the tibial component, the contact points moving in a posterior direction relative to the tibial component upon flexion of the femoral and tibial components due to contact between the cam surface and the engaging means from about 25 degrees flexion to about 45 degrees flexion, and the contact points remaining in a constant position relative to the tibial component upon flexion of the femoral and tibial components from about 45 degrees to the flexed position.

3. The prosthesis of claim 2, wherein the tibial component includes an anterior end, a posterior end, and a medial/lateral center line extending across the tibial component midway between the anterior and posterior ends, the total distance of movement of the contact points in the posterior direction of the center line upon flexion of the femoral and tibial components from about 25 degrees flexion to the flexed position being about 6 mm.

4. A knee joint prosthesis comprising:

a femoral component including first and second spaced apart, convexly curved condyle bearing surfaces and a cam surface extending between the first and second bearing surfaces; and a tibial component, the femoral component being articulatable with the tibial component between an extended position and a flexed position, the tibial component including first and second bearing surfaces for engaging the first and second bearing surfaces of the femoral component, respectively, and means for engaging the cam surface of the femoral component to control the position of the femoral component relative to the tibial component only upon flexion of the femoral and tibial components between about 25 degrees and the flexed position, the cam surface being spaced apart from the engaging means upon flexion of the femoral and tibial components between the extended position and about 25 degrees, wherein the engaging means includes a stabilizing post extending away from the tibial component between the first and second bearing surfaces, the stabilizing post having a posterior side wall including a first inferior section sloped downwardly in the posterior direction for engaging the cam surface of the femoral component to control the position of the femoral component relative to the tibial component upon flexion of the femoral and tibial components between about 25 degrees and the flexed position and including a second superior section aligned generally perpendicularly to the first and second bearing surfaces of the tibial component to engage the cam surface of the femoral component upon posterior movement of the tibial component relative to the femoral component to prevent dislocation of a contact point between the femoral and tibial components.

5. The prosthesis of claim 4, wherein the cam surface of the femoral component includes a generally concave contact surface and the posterior side wall of the stabilizing post includes a generally convex contact surface.

6. A knee joint prosthesis comprising:

a femoral component including first and second spaced apart, convexly curved, condyle bearing surfaces and a cam surface extending between the first and second bearing surfaces; and a tibial component, the femoral component being articulatable with the tibial component between an extended position and a flexed position, the tibial component including first and second bearing surfaces for engaging the first and second bearing surfaces of the femoral component, respectively, and a stabilizing post having a posterior side wall including a first inferior uncurved straight section sloped downwardly in the posterior direction for engaging the cam surface of the femoral component to control the position of the femoral component relative to the tibial component upon flexion of the femoral and tibial components and including a second superior section aligned generally perpendicularly to the first and second bearing surfaces of the tibial component to engage the cam surface of the femoral component upon posterior movement of the tibial component relative to the femoral component to prevent dislocation of the femoral and tibial components.

7. The prosthesis of claim 6, wherein the cam surface of the femoral component includes a generally concave contact surface and the posterior side wall includes a generally convex contact surface.

8. The prosthesis of claim 6, wherein the cam surface is spaced apart from the posterior side wall of the stabilizing post upon flexion of the femoral and tibial components between the extended position and about 25 degrees and the stabilizing post engages the cam surface of the femoral component only after about a 25 degree flexion of the femoral and tibial components.

9. A knee prosthesis comprising:
   a femoral component including first and second spaced apart, convexly curved condyle bearing surfaces and a cam surface extending between the first and second bearing surfaces; and
   a tibial component, the femoral component being articulatable with the tibial component between an extended position and a flexed position, the tibial component including an anterior/posterior axis and first and second bearing surfaces situated on opposite sides of the anterior/posterior axis for engaging the first and second bearing surfaces of the femoral component, respectively, at first and second contact points located at substantially equal positions relative to the anterior/posterior axis of the tibial component, the tibial component also including a stabilizing post having a posterior side wall for engaging the cam surface of the femoral component only after about a 25 degree flexion of the femoral and tibial components, the contact points between the bearing surfaces of the tibial and femoral components moving in a posterior direction due to contact between the posterior side wall and the cam surface upon flexion of the tibial and femoral components between about 25 degrees and about 45 degrees and the contact points remaining in a constant dwell positions relative to the tibial component upon flexion of the tibial and femoral components between about 45 degrees flexion and the flexed position.

10. The prosthesis of claim 9, wherein the total distance of movement of the contact points in the posterior direction during flexion of the tibial and femoral components from the extended position to the flexed position is less than 9 mm.

11. The prosthesis of claim 9, wherein the cam surface of the femoral component includes a generally concave contact surface and the posterior side wall includes a generally convex contact surface.

12. A knee joint prosthesis comprising:
   a femoral component including first and second spaced apart, convexly curved condyle bearing surfaces and a cam surface extending between the first and second bearing surfaces; and
   a tibial component, the femoral component being articulatable with the tibial component between an extended position and a flexed position, the tibial component including an anterior end, a posterior end, an anterior/posterior axis extending between the anterior and posterior ends, and a medial/lateral center line extending across the tibial component midway between the anterior and posterior ends, the tibial component including first and second bearing surfaces for engaging the first and second bearing surfaces of the femoral component, respectively, at first and second contact points located at substantially equal positions relative to the anterior/posterior axis of the tibial component, the tibial component also including means for engaging the cam surface of the femoral component to control the position of the femoral component relative to the tibial component upon flexion of the femoral and tibial components only between about a 25° flexion angle and the flexed position, the contact points moving in a posterior direction relative to the tibial component to a predetermined location about 6 mm in the posterior direction of the center line of the tibial component upon flexion of the tibial and femoral components from about 25 degrees to about 45 degrees and the contact points remaining at the same predetermined location of about 6 mm in the posterior direction of the center line upon flexion of the tibial and femoral components from about 45 degrees to the flexed position.

13. The prosthesis of claim 12, wherein the contact points are situated substantially on the center line of the tibial component when the femoral and tibial components are flexed at an angle of about 30 degrees.

14. The prosthesis of claim 12, wherein the engaging means includes a stabilizing post extending away from the tibial component between the first and second bearing surfaces, the stabilizing post having a posterior side wall including a first inferior section sloped downwardly in the posterior direction for engaging the cam surface of the femoral component to control the position of the femoral component relative to the tibial component upon flexion of the femoral and tibial components between about 25 degrees and the flexed position and including a second superior section aligned to lie generally perpendicularly to the first and second bearing surfaces of the tibial component to engage the cam surface of the femoral component upon posterior movement of the tibial component relative to the femoral component to prevent dislocation of the femoral and tibial components.

15. A knee joint prosthesis comprising:
   a femoral component including first and second spaced apart, convexly curved condyle bearing surfaces, an anterior cam surface extending between the first and second bearing surfaces, and a posterior cam surface extending between the first and second bearing surfaces; and
   a tibial component, the femoral component being articulatable with respect to the tibial component between an extended position and a flexed position, the tibial component including an anterior/posterior axis and first and second bearing surfaces located on opposite sides of the anterior/posterior axis for engaging the first and second bearing surfaces of the femoral component, respectively, at first and second contact points located at substantially equal positions relative to the anterior/posterior axis of the tibial component, the tibial component also including a stabilizing post having a posterior side wall for engaging the posterior cam surface of the femoral component to control the position of the femoral component relative to the tibial component only upon flexion of the femoral and tibial components between about 25 degrees and the flexed position and having an anterior side wall for engaging the anterior cam surface upon about a 5 degree hyperextension of the tibial and femoral components, the anterior and posterior cam surfaces being spaced apart from the anterior and posterior side walls, respectively, of the stabilizing post upon flexion of the femoral and tibial components between about 5 degrees hyperextension and about 25 degrees flexion to permit free movement of the femoral component relative to the tibial component.

16. The prosthesis of claim 15, wherein the posterior side wall of the stabilizing post includes a first inferior section sloped downwardly in the posterior direction for engaging the posterior cam surface of the femoral component to control the position of the femoral component relative to the tibial component upon flexion of the femoral and tibial components between about 25 degrees and the flexed position, the posterior side wall also including a second superior section aligned to lie generally perpendicularly to the first and second bearing surfaces of the tibial component to engage the posterior cam surface of the femoral component upon posterior movement of the tibial component relative to the femoral component to prevent dislocation of the femoral and tibial components.

17. The prosthesis of claim 15, wherein the posterior cam surface of the femoral component includes a generally concave contact surface in the posterior side wall of the stabilizing post includes a generally convex contact surface.

18. A knee joint prosthesis comprising:
a tibial component includes first and second bearing surfaces and a stabilizing post having a posterior side wall including a generally convex contact surface located between the first and second bearing surfaces; and
a femoral component articulatable with the tibial component between an extended position and a flexed position, the femoral component including first and second spaced apart, convexly curved condyle bearing surfaces for engaging the first and second bearing surfaces of the tibial component, respectively, and a generally concave cam surface extending between the first and second bearing surfaces of the femoral component for engaging the convex contact surface of the posterior side wall of the stabilizing post to control the position of the femoral component relative to the tibial component only upon flexion of the femoral and tibial components from about 25° flexion to the flexed position, and wherein the control provides for a point of contact between the femoral and tibial components to move in a posterior direction from about 25 degrees through 45 degrees and to remain substantially unchanged from about 45 degrees to the flexed position.

19. A knee joint prosthesis comprising:
a femoral component including first and second spaced apart, convexly curved condyle bearing surfaces and a cam surface extending between the first and second bearing surfaces; and
a tibial component, the femoral component being articulatable with the tibial component between an extended position and a flexed position, the tibial component including first and second bearing surfaces for engaging the first and second bearing surfaces of the femoral component, respectively, and means for engaging the cam surface of the femoral component to control the position of the femoral component relative to the tibial component only upon flexion of the femoral and tibial components between about 25 degrees and the flexed position, the cam surface being spaced apart from the engaging means upon flexion of the femoral and tibial components between the extended position and about 25 degrees, wherein the posterior side wall of the tibial component includes a first inferior section sloped downwardly in the posterior direction for engaging the cam surface of the femoral component to control the position of the femoral component relative to the tibial component only upon flexion of the femoral and tibial components from about 25 degrees to the flexed position, the posterior side wall also including a second superior section aligned generally perpendicularly to the first and second bearing surfaces of the tibial component to engage the cam surfaces of the femoral component upon posterior movement of the tibial component relative to the femoral component to prevent dislocation of a contact point between the femoral and tibial components.

20. The prosthesis of claim 19, wherein the cam surface of the femoral component has the shape of a hyperboloid.

* * * * *